United States Patent
Sohn et al.

(10) Patent No.: US 10,219,089 B2
(45) Date of Patent: Feb. 26, 2019

(54) HEARING LOSS COMPENSATION APPARATUS AND METHOD USING 3D EQUAL LOUDNESS CONTOUR

(71) Applicant: SAMSUNG ELECTRONICS CO., LTD., Suwon-si (KR)

(72) Inventors: Jun Il Sohn, Yongin-si (KR); Dong Wook Kim, Seoul (KR); Yun Seo Ku, Seoul (KR); Jong Jin Kim, Hwaseong-si (KR); Jun Whon Uhm, Anyang-si (KR); Jong Min Choi, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 901 days.

(21) Appl. No.: 14/156,780

(22) Filed: Jan. 16, 2014

(65) Prior Publication Data

US 2014/0211971 A1 Jul. 31, 2014

(30) Foreign Application Priority Data

Jan. 29, 2013 (KR) .................. 10-2013-0009747

(51) Int. Cl.
*H04R 25/00* (2006.01)
*A61B 5/12* (2006.01)

(52) U.S. Cl.
CPC ............. *H04R 25/70* (2013.01); *A61B 5/123* (2013.01); *H04R 25/407* (2013.01)

(58) Field of Classification Search
CPC ...................................................... H04R 25/70
See application file for complete search history.

(56) References Cited

U.S. PATENT DOCUMENTS

| 4,099,035 | A  | * | 7/1978  | Yanick  | H03G 9/025 381/106 |
| 6,987,856 | B1 | * | 1/2006  | Feng    | G01S 3/8083 367/124 |
| 7,206,423 | B1 | * | 4/2007  | Feng    | H04B 13/005 381/312 |
| 7,860,262 | B2 | * | 12/2010 | Drtina  | G01S 3/807 381/23.1 |

(Continued)

OTHER PUBLICATIONS

Guanming Lu et al., Digital Audio Principles and Applications Second Edition, Aug. 31, 2012, pp. 11-12, Beijing: China Machine Press.

(Continued)

*Primary Examiner* — Matthew A Eason
*Assistant Examiner* — Taunya McCarty
(74) *Attorney, Agent, or Firm* — Jefferson IP Law, LLP

(57) ABSTRACT

A hearing loss compensation apparatus and method compensate for distortion caused by a change in a sound transmission path using hearing characteristics of a user. The hearing loss compensation apparatus may include a sound direction detection device configured to detect a sound generation direction, in which a sound generates, using one or more microphones, and a sound compensation device configured to compensate the sound using hearing characteristics of a user corresponding to the sound generation direction. Additionally, a hearing characteristics measurement apparatus and method provide a way to obtain such hearing characteristics information.

7 Claims, 8 Drawing Sheets

(56) References Cited

U.S. PATENT DOCUMENTS

| | | | | |
|---|---|---|---|---|
| 8,130,989 B2* | 3/2012 | Latzel | ................... | H04R 25/70 |
| | | | | 381/312 |
| 2007/0223752 A1* | 9/2007 | Boretzki | ................ | H04R 25/70 |
| | | | | 381/312 |
| 2009/0132275 A1* | 5/2009 | Jung | ........................ | A61B 5/16 |
| | | | | 705/2 |
| 2010/0257128 A1* | 10/2010 | De Vries | ................ | A61B 5/121 |
| | | | | 706/12 |
| 2010/0310101 A1* | 12/2010 | Anderson | ................ | A61B 5/11 |
| | | | | 381/309 |
| 2011/0075853 A1 | 3/2011 | Anderson | | |
| 2011/0142272 A1* | 6/2011 | Takagi | ................... | A61B 5/121 |
| | | | | 381/321 |
| 2012/0132004 A1* | 5/2012 | Ito | ......................... | A61B 5/123 |
| | | | | 73/585 |
| 2013/0339025 A1* | 12/2013 | Suhami | ................. | H04R 25/00 |
| | | | | 704/271 |

OTHER PUBLICATIONS

Chinese Office Action dated Oct. 12, 2018, issued in Chinese Patent Application No. 201410042788.2.

* cited by examiner

HEARING LOSS COMPENSATION APPARATUS AND METHOD USING 3D EQUAL LOUDNESS CONTOUR

CROSS-REFERENCE TO RELATED APPLICATION(S)

This application claims the benefit under 35 USC § 119(a) of Korean Patent Application No. 10-2013-0009747 filed on Jan. 29, 2013, in the Korean Intellectual Property Office, the entire disclosure of which is incorporated herein by reference for all purposes.

BACKGROUND

1. Field

The following description relates to an apparatus and method for compensating for hearing loss, and to an apparatus and method for compensating for a distortion, caused by a change in a sound transmission path, by using a 3-dimensional (3D) equal loudness contour.

2. Description of Related Art

A patient with hearing loss may be unable to hear portions of surrounding sound that a person with normal hearing would be able to hear. A hearing loss compensation apparatus compensates for parts of surrounding sound that a hearing loss patient cannot hear and provides the compensated sound to the hearing loss patient, so that the hearing loss patient may normally perceive the sound.

However, since the hearing loss compensation apparatus is worn on an ear of the hearing loss patient, the sound transmission path from a sound generation place to an eardrum may be changed. For example, such a hearing loss compensation apparatus may move around with respect to its position relative to the eardrum. When such a change occurs, the sound to be heard by the hearing loss patient may be distorted due to effects resulting from the changes in position of the apparatus. Therefore, it may be difficult for the hearing loss patient to identify a direction of sound.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a hearing loss compensation apparatus includes a sound direction detection device configured to detect a sound generation direction, from which a sound is generated, using one or more microphones, and a sound compensation device configured to compensate the sound using hearing characteristics of a user corresponding to the sound generation direction.

The hearing characteristics of the user may include a 3-dimensional (3D) equal loudness contour of the user, determined by mapping hearing thresholds corresponding to azimuths and frequencies on a 2D plane defined by an azimuth and a frequency.

The hearing threshold may be a minimum magnitude of sound audible by the user, for an azimuth and frequency, which is measured by moving a position of a sound stimulation for measurement of hearing capability to change an azimuth of the user and by controlling a frequency and a magnitude of the sound stimulation.

The sound compensation device may be configured to determine the hearing characteristics of the user by comparing hearing abilities of the user at the azimuths and average hearing abilities of other users at the respective azimuths, and amplify the sound based on a characteristic, among the hearing characteristics of the user, that corresponds to an azimuth corresponding to the sound generation direction.

In another general aspect, a hearing characteristics measurement apparatus includes a hearing threshold determination device configured to determine hearing thresholds corresponding to magnitudes, frequencies, and output positions of sound stimulations, and a hearing characteristic determination device configured to determine a 3-dimensional (3D) equal loudness contour of a user, by mapping the hearing thresholds on a 2D plane defined by a frequency and an azimuth.

The hearing threshold determination device may include a sound stimulation change device configured to change a magnitude, a frequency, and an output position of a sound stimulation, and a hearing threshold measurement device configured to measure a hearing threshold corresponding to the changed sound stimulation, based on a user input.

In another general aspect, a hearing loss compensation method includes detecting a sound generation direction, from which a sound is generated, using one or more microphones, and compensating the sound using hearing characteristics of a user corresponding to the sound generation direction.

The hearing characteristics of the user may include a 3-dimensional (3D) equal loudness contour of the user, determined by mapping hearing thresholds corresponding to azimuths and frequencies on a 2D plane defined by an azimuth and a frequency.

The hearing threshold may be a minimum magnitude of sound audible by the user, for an azimuth and frequency, which is measured by moving a position of a sound stimulation for measurement of hearing capability to change an azimuth of the user and controlling a frequency and a magnitude of the sound stimulation.

The compensating may include determining the hearing characteristics of the user by comparing hearing abilities of the user at the azimuths and average hearing abilities of other users at the respective azimuths, and amplifying the sound based on a characteristic among the hearing characteristics of the user, that corresponds to an azimuth corresponding to the sound generation direction.

In another general aspect, a non-transitory computer readable storage medium may store a program for hearing loss compensation, the program comprising instructions for causing a computer to implement the method of hearing loss compensation presented above.

In another general aspect, a hearing characteristics measurement method includes determining hearing thresholds corresponding to magnitudes, frequencies, and output positions of sound stimulations; and determining a 3-dimensional (3D) equal loudness contour of a user, by mapping the hearing thresholds on a 2D plane defined by a frequency and an azimuth.

The determining the threshold may include changing a magnitude, a frequency, and an output position of a sound stimulation, and measuring a hearing threshold corresponding to the changed sound stimulation, based on a user input.

In another general aspect, anon-transitory computer readable storage medium may store a program for hearing characteristics measurement, the program comprising instructions for causing a computer to implement the method of hearing characteristics measurement presented above.

In another general aspect, a hearing characteristics measurement apparatus includes a sound stimulation output device, configured to produce sound stimulations with different magnitudes, frequencies and output positions and a hearing threshold determination device configured to determine hearing thresholds corresponding to magnitudes, frequencies, and output positions of the sound stimulations.

The hearing characteristics measurement apparatus may further include a hearing characteristic determination device configured to determine a 3-dimensional (3D) equal loudness contour of a user, by mapping the hearing thresholds on a 2D plane defined by a frequency and an azimuth.

The sound stimulation output device may adjust magnitudes of a sound stimulation at a fixed frequency and output position until the hearing threshold determination determines a hearing threshold.

The sound stimulation output device, after finding a hearing threshold at a fixed frequency and output position, may find hearing thresholds at other frequencies for that output position.

The sound stimulation output device, after finding a hearing threshold at a fixed frequency and output position, may find hearing thresholds at other output positions for that frequency.

Other features and aspects will be apparent from the following detailed description, the drawings, and the claims.

Figure 1:
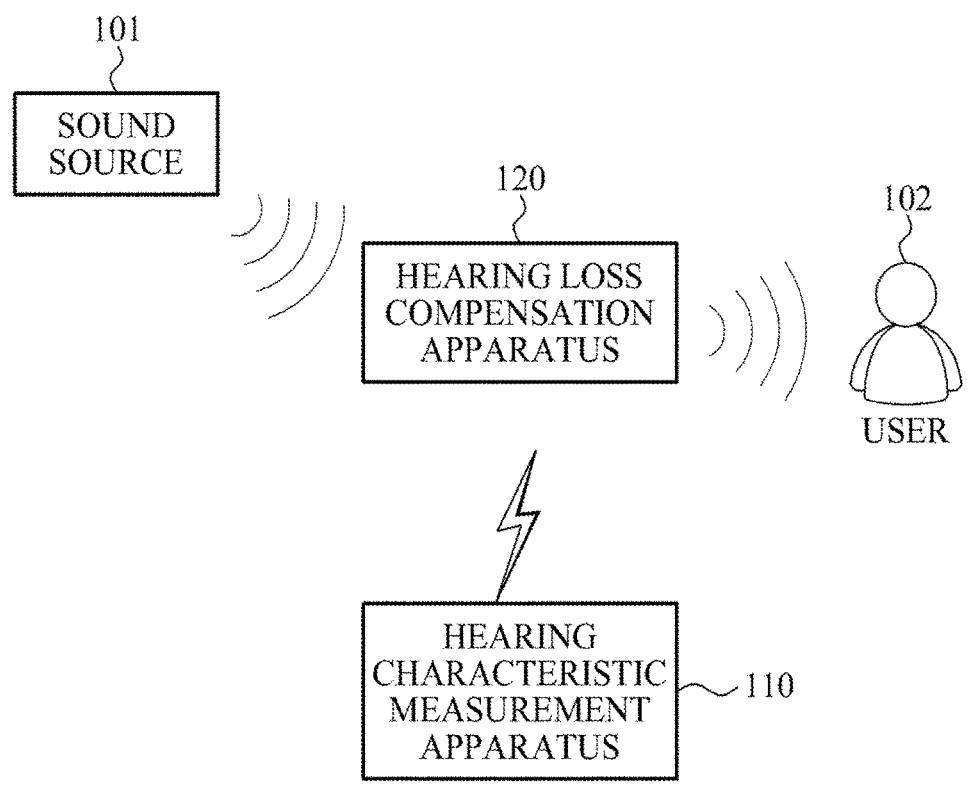
FIG. 1 is a diagram illustrating an example of operation of a hearing loss compensation apparatus, according to an example embodiment.

Throughout the drawings and the detailed description, unless otherwise described or provided, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Based on the difficulties discussed above involved in identifying a direction of sound by patients with hearing loss, there is a need for a hearing loss compensation method. Such a method compensates for the distortion caused by the change in the sound transmission path by using a hearing loss compensation apparatus to help manage the distortion, as will be discussed further, below. As used herein, the term "compensates" and "compensating" with respect to a sound refers to processing the sound to modify the characteristics of the sound so that a user with hearing impairment is able to hear the sounds as if that user did not have impaired hearing. Thus, a "compensated" sound may be adjusted to take into account discrepancies between a user's hearing characteristics and expected or average hearing characteristics.

FIG. 1 is a diagram illustrating an example of operation of a hearing loss compensation apparatus 120, according to an example embodiment.

The hearing loss compensation apparatus 120 performs a compensation operation on a sound generated by a sound source 101 according to hearing characteristics of a user 102. For example, the hearing characteristics of the user 102 are measured by a hearing characteristic measurement apparatus 110. After the compensation operation occurs, the hearing loss compensation apparatus outputs the compensated sound to the user 102.

In this example, the hearing characteristics of the user 102 are a 3-dimensional (3D) equal loudness contour of the user 102. An example way to obtain the equal loudness contour of the user 102 is to determine the equal loudness contour by mapping hearing thresholds corresponding to azimuths and frequencies on a 2D plane defined by the azimuth and the frequency. However, other appropriate mathematical analysis techniques that provide a similar equal loudness contour may be used to provide the equal loudness contour for output to the user.

The sound source 101 is a source of sounds collected by the hearing loss compensation apparatus 120 by a microphone or another sound reception sensor. For example, the sound source 101 may include an electronic device that outputs sound such as a loudspeaker, a person speaking around the user, a crying animal, and a device making a driving sound. However, these are only examples of a sound source 101, and are not intended as limiting the types of sound source 101 that may be collected by the hearing loss compensation apparatus 120. Furthermore, in addition to collecting the content of the signal, microphone or other sound reception sensor may gather information indicative of the directionality of the sound, such as the physical location of the sound source and how the sound signal is distributed in three dimensions.

Thus, the hearing loss compensation apparatus 120 compensates for distortions included in the sound generated from the sound source 101 using the 3D equal loudness contour of the user. When the user 102 wears the hearing loss compensation apparatus 120, distortion of sound generated, such as when a head related transfer function (HRTF) which is one of sound transmission paths is changed, is compensated for by the hearing loss compensation apparatus 120.

Figure 2:
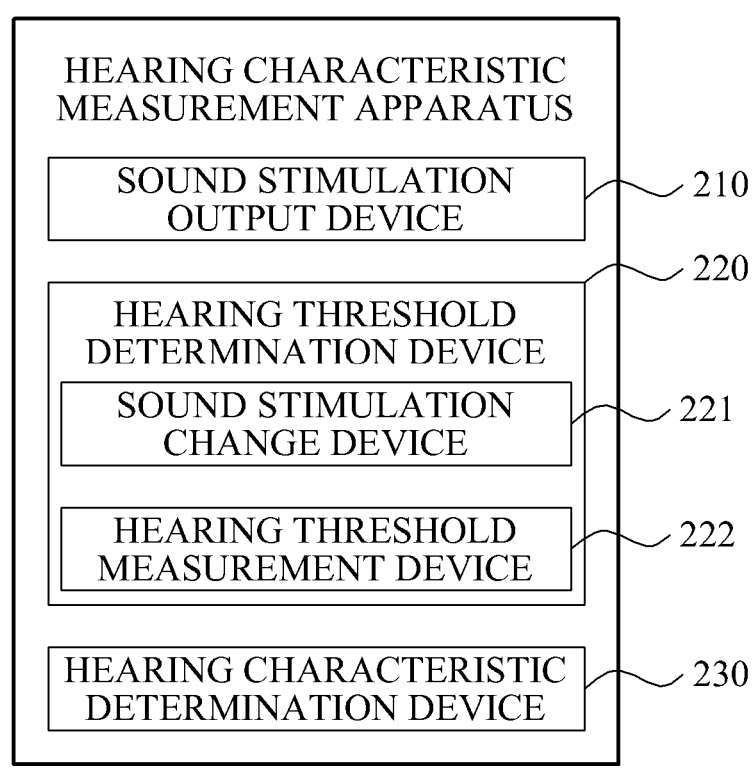
FIG. 2 is a diagram illustrating a configuration of an example of a hearing characteristic measurement apparatus, according to an example embodiment.

FIG. 2 is a diagram illustrating a configuration of an example of a hearing characteristic measurement apparatus 110, according to an example embodiment.

Referring to FIG. 2, the hearing characteristic measurement apparatus 110 may include a sound stimulation output device 210, a hearing threshold determination device 220, and a hearing characteristic determination device 230.

The sound stimulation output device 210 outputs sound stimulation for measuring the 3D equal loudness contour of the user. For example, the sound stimulation refers to an arbitrary predetermined sound that the user perceives. Such a sound may be used to stimulate the hearing of the user. As will be discussed further below, as the sound stimulation is varied, the user can provide information about how he or she perceives the sound stimulation, thereby allowing gathering of information about how the user perceives sound with different characteristics.

The hearing threshold determination device 220 determines hearing thresholds corresponding to magnitudes, frequencies, and output positions of the sound stimulations output by the sound stimulation output device 210. For example, the output positions of the sound stimulations may be at equal distances from the user while azimuths are different. While the sound stimulations are equally far from the user, if there are different azimuths the sound stimulations will be incident upon the user from different directions. As discussed above, one of the goals of the present technology is to help provide a user with hearing impairment with the ability to discriminate between sounds coming from different directions. Hence, by determining hearing thresholds incident from a variety of positions helps to establish which aspects of the user's hearing need to be compensated for.

The hearing threshold determination device 220 may change the magnitude, the frequency, and the output position of the sound stimulation, and measure a hearing threshold corresponding to the changed magnitude, frequency, and output position of the sound stimulation.

For example, as shown in FIG. 2, the hearing threshold determination device 220 may include a sound stimulation change device 221 and a hearing threshold measurement device 222.

The sound stimulation change device 221 changes the magnitude, the frequency, the output position of the sound stimulation by controlling the sound stimulation output device 210. By changing these aspects of the sound stimulation, the sound stimulation change device 221 is able to provide varying sound stimulation that allows the hearing threshold determination device 220 to assess characteristics of the hearing of the user to determine what must be done to the sound to compensate for hearing deficits of the user.

The hearing threshold measurement device 222 measures the hearing threshold corresponding to the sound stimulation, as the sound stimulation is changed by the sound stimulation change device 221, based on a user input.

In one example, the sound stimulation change device 221 changes the magnitude of the sound stimulation while keeping constant the frequency and the output position of the sound stimulation. In this example, when the user does not perceive the sound stimulation, the user inputs that the user cannot perceive the sound using a switch or another input device. While a switch is an example of such an input device, any input device that allows the user to indicate that he or she cannot perceive the sound may be used. Additionally, in an embodiment a user may also be able to provide quantitative information related to the sound such as an indication of loudness or pitch, which such an embodiment uses to further characterize the hearing of the user. In addition, upon the user input, the hearing threshold measurement device 222 may measure the magnitude of the sound stimulation output by the sound stimulation output device 210 as the hearing threshold of the user at the fixed frequency and position. That is, the sound stimulation output device 210 progressively changes the sound stimulation it outputs, until the user can no longer hear the sound stimulation. By obtaining such information by interaction with the user, the hearing threshold determination device 220 can establish characteristics about what the user is able to hear.

Next, the sound stimulation change device 221 changes one of the frequency and the output position of the sound stimulation and then changes the magnitude of the sound stimulation. By making this change, the sound stimulation change device 221 is able to characterize the relationship between sound magnitude and the ability of the user to hear sounds with different characteristics, such as different frequencies or positions. Thereafter, the hearing threshold measurement device 222 waits for the user input as discussed above. Upon the user input, the hearing threshold measurement device 222 measures the magnitude of the sound stimulation output by the sound stimulation output device 210 as the hearing threshold of the user at the changed frequency and position.

The hearing threshold determination device 220 repeats the above process for predetermined groups of frequencies and output positions. For example, the hearing threshold determination device 220 repeats the above process for every predetermined frequency and output position of the sound stimulation included in the groups, thereby determining hearing thresholds corresponding to all frequencies and azimuths. In an alternative embodiment, the hearing threshold determination device 220 only repeats the above process for a subset of frequencies and output positions. When data is obtained only for a subset of frequencies and output positions, various techniques may be used to provide approximations as a replacement for missing data.

Figure 3:
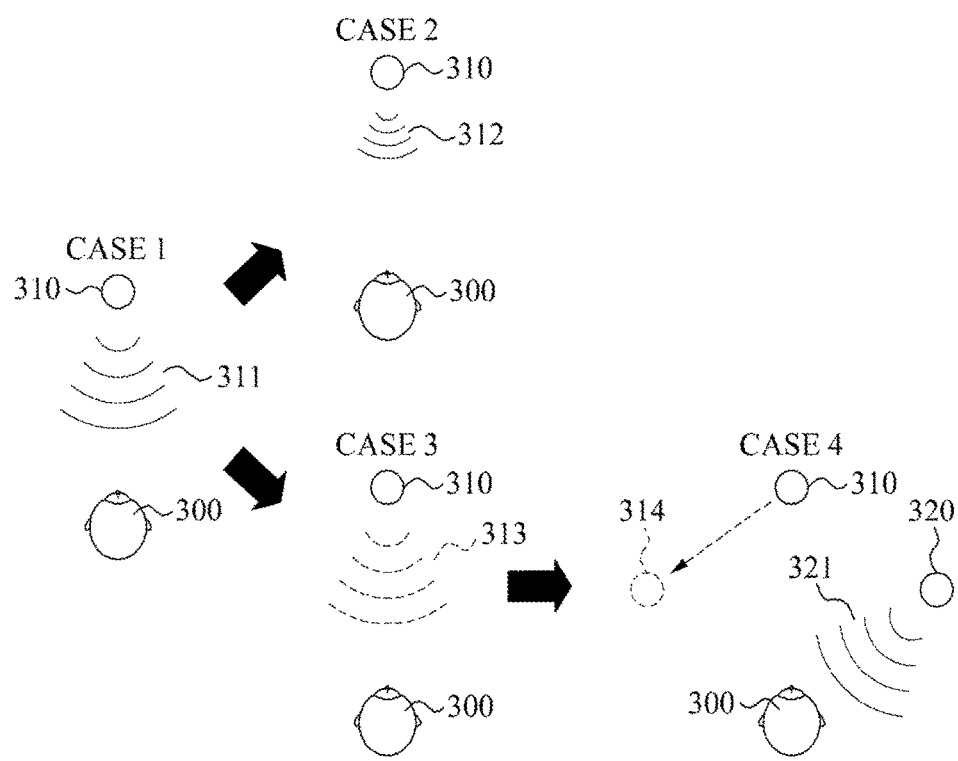
FIG. 3 is a diagram illustrating an example of operation of a hearing characteristic measurement apparatus, according to an example embodiment.

The hearing characteristic determination device 230 determines the 3D equal loudness contour of the user, by mapping the hearing thresholds determined by the hearing threshold determination device 220 on the 2D plane defined by the frequency and the azimuth. FIG. 3 is a diagram illustrating an example of operation of a hearing characteristic measurement apparatus, according to an example embodiment.

First, the sound stimulation change device 221 may output a sound stimulation 311 of a predetermined frequency from the sound stimulation output device 310 located in front of a user 300 as shown in the example of Case 1 as in a noiseless space. In this example, a noiseless space permits accurate hearing threshold measurement.

The hearing threshold measurement device 222 receives input as information from the user, the information indicating whether the user 300 perceived the sound stimulation 311.

For example, the user 300 may hold a switch and press the switch only when he or she cannot perceive the sound stimulation 311, thereby inputting the information that the user 300 has not perceived the sound stimulation 311 to the hearing threshold measurement device 222. Here, when the hearing threshold measurement device 222 does not receive any input from the user 300 for a predetermined time, it may be determined that the user 300 has perceived the sound stimulation 311. By gathering such information, an embodiment is able to establish the boundaries about the magnitude of sound stimulation 311 that is necessary for the user 300 to be able to hear sound under certain conditions.

Alternatively, it is possible to determine whether the user is able to perceive the sound in an alternative manner, such as by having the user press the switch as soon as he or she is able to perceive the sound stimulation 311. Similarly, the user 300 may input any one selected from information that the user 300 has perceived the sound stimulation 311 and the information that the user 300 has not perceived the sound stimulation 311. Any input device that allows the user 300 to indicate that the magnitude change has caused a transition from the user 300 not being able to perceive the sound stimulation 311 may be used in such an embodiment.

In an example, the sound stimulation change device 221 controls the sound stimulation output device 210 according to the user input.

In an example, the hearing device measurement device 222 does not receive any input from the user 300 for the predetermined time or receives the information that the user 300 has perceived the sound stimulation 311 from the user 300. Here, the sound stimulation change device 221 determines that magnitude of the sound stimulation 311 is greater than the hearing threshold of a predetermined frequency in front of the user, as previously determined, and therefore reduces the magnitude of the sound stimulation 311. For example, the sound stimulation output device 210 outputs a sound stimulation 312 whose magnitude is reduced by the sound stimulation change device 221 as shown in Case 2 in FIG. 3. In another example, when the hearing threshold measurement device 222 receives input that the user 300 has not perceived the sound stimulation 311 from the user 300, the hearing threshold determination device 220 operates as shown in Case 3 in FIG. 3.

In another example, the hearing threshold measurement device 222 receives the information that the user 300 no longer perceives the sound stimulation 311. In this case, the hearing threshold measurement device 222 determines and measures the magnitude of the sound stimulation 311 as the hearing threshold in front of the user.

In an additional example, the sound stimulation change device 221 changes a frequency of the sound stimulation so that the hearing threshold measurement device 222 measures a hearing threshold of another frequency. Here, the sound stimulation output device 210 may output a sound stimulation 313 whose frequency is changed by the sound stimulation change device 221 as shown in Case 3 in FIG. 3. The magnitude of the sound stimulation 313 output by the sound stimulation output device 210 may be a default value or a value measured as the hearing threshold in Case 1.

In an embodiment, the hearing threshold determination device 220 repeats operations of Case 1 to Case 3, as discussed, until the hearing thresholds of the user with respect to all candidate frequencies are measured.

In an additional example, when the hearing thresholds of the user with respect to all the frequencies are measured from a position in front of the user, the hearing threshold determination device 220 changes an output position of the sound stimulation.

For example, the hearing threshold determination device 220 measures a hearing threshold corresponding to an azimuth of the user. The azimuth of the user refers to the angle between projected vectors in a horizontal plane directed towards a new position of the sound stimulation output device and an original position of the sound stimulation output. The hearing threshold determination device 220 measures the hearing threshold by having the sound stimulation output device 320 located in a position 314, in which the azimuth is changed with respect to the user 300 as shown in Case 4, output a sound stimulation 321. Here, the hearing threshold determination device 220 repeats the operations of Case 1 to Case 3 by changing the magnitude and the frequency of the sound stimulation output by the sound stimulation output device 320 in the new position 314. By doing so, the hearing threshold determination device 220 measures the hearing thresholds corresponding to the respective frequencies at the azimuth of the user.

In addition, the hearing threshold determination device 220 may move the sound stimulation output device 310 to the position 314 in which the azimuth is changed with respect to the user 300 as shown in Case 4, and have the sound stimulation output device 310 output the sound stimulation, thereby measuring the hearing threshold corresponding to the azimuth of the user.

Figure 4:
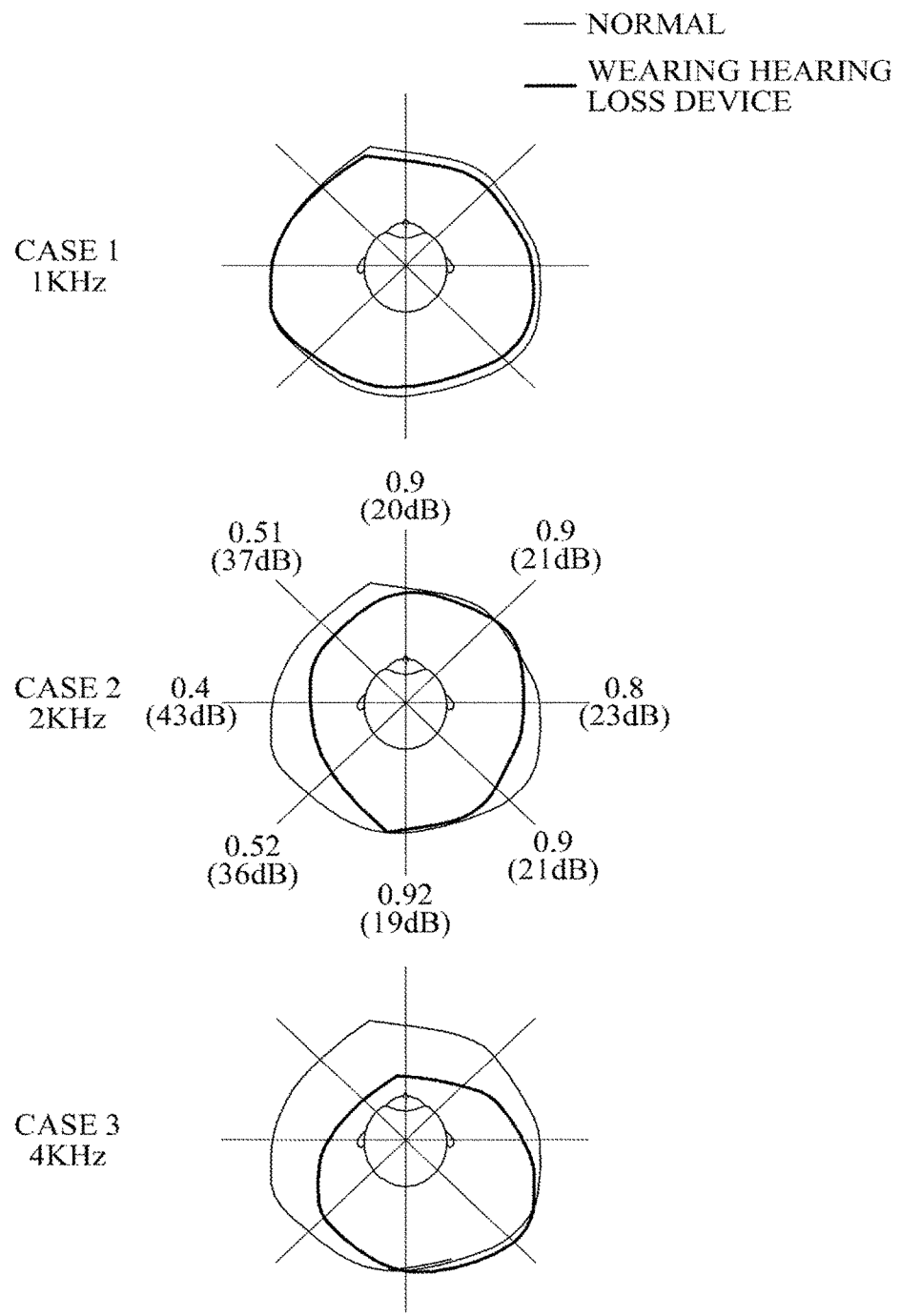
FIG. 4 is a diagram illustrating an example of an equal loudness contour according to frequencies, according to an example embodiment.

FIG. 4 illustrates an example of an equal loudness contour according to frequencies, according to an example embodiment.

FIG. 4 illustrates an example of measuring equal loudness contours per frequency of a normal user and equal loudness contours per frequency of a user wearing a hearing device. In an example, the hearing device is the hearing loss compensation apparatus 120.

As shown in Case 1 of FIG. 4, the equal loudness contour per frequency of the normal user and the equal loudness contour per frequency of the user wearing the hearing device may be similar at a particular frequency, for example, about 1 KHz. At this frequency contour shows that at this frequency, hearing by the normal user and the user wearing the hearing device are similar. Accordingly, the hearing loss compensation apparatus 120 may not compensate a sound having the frequency of about 1 KHz. In this case, the user wearing the hearing device effectively has normal hearing, and hence correction of such sounds is not necessary.

However, as shown in Case 2 and Case 3, the equal loudness contour per frequency of the normal user and the equal loudness contour per frequency of the user wearing the hearing device may be different at particular frequencies such as about 2 KHz and about 4 KHz.

Therefore, when the frequency of the sound is about 2 KHz, the hearing loss compensation apparatus 120 may compensate the sound based on the difference between the equal loudness contour per frequency of the normal user and the equal loudness contour per frequency of the user wearing the hearing device, shown in Case 2 of FIG. 4. In FIG. 4, Case 2 also illustrates information about the how the equal loudness contour per frequency of the normal user and the equal loudness contour per frequency of the user wearing the hearing device relate to one another. For example, Case 2 provides, for different azimuths, a ratio provided as a decimal value between 0 and 1 and a magnitude in dB in parentheses. In an example, the information from case 2 at a given azimuth indicates a ratio between the magnitudes of the equal loudness contours differ for that azimuth, and the magnitude in dB in parentheses is a measure of the magnitude in dB that produces a signal of equal loudness for the normal user and the user wearing the hearing device.

When the frequency of the sound is about 4 KHz, the hearing loss compensation apparatus 120 may compensate the sound based on the difference between the equal loudness contour per frequency of the normal user and the equal loudness contour per frequency of the user wearing the hearing device, shown in Case 3 of FIG. 4. While Case 3 of FIG. 4 does not include a listing of the same information that is provided in Case 2, it is similar in that by comparing the equal loudness contour per frequency of the normal user and the equal loudness contour per frequency of the user wearing the hearing device, an embodiment is able to determine how to compensate for hearing deficits of the user wearing the hearing device based on measured characteristics of the loudness contours. For example, at 4 KHz, the user wearing the hearing device has relatively normal hearing from behind and to the right, but compensation is necessary for sounds of this frequency ahead of and to the left of the user.

Figure 5:
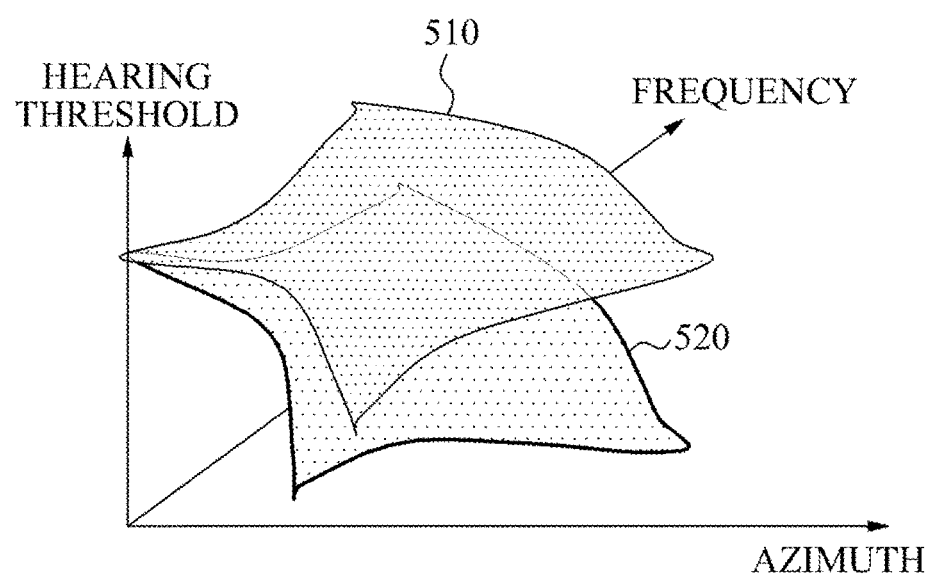
FIG. 5 is a diagram illustrating an example of a 3-dimensional (3D) equal loudness contour of a user, according to an example embodiment.

FIG. 5 illustrates an example of a 3D equal loudness contour of a user, according to an example embodiment.

In an embodiment, the 3D equal loudness contour of the user, determined by the hearing characteristic measurement apparatus 110, is expressed by 3D information disposed in a 3D space including axes respectively of an azimuth, a frequency, and a hearing threshold as shown in FIG. 5.

For example, the hearing characteristic measurement apparatus 110 determine the 3D equal loudness contour of the user, by mapping a value of a hearing threshold as height on a 2D plane defined by the frequency and the azimuth.

In an example, the equal loudness contour per frequency of the normal user and the equal loudness contour per frequency of the user wearing the hearing device differ as shown in FIG. 4.

Accordingly, a 3D equal loudness contour 510 of the normal user and a 3D equal loudness contour 520 of the user wearing the hearing device may be distinguished as shown in FIG. 5.

Figure 6:
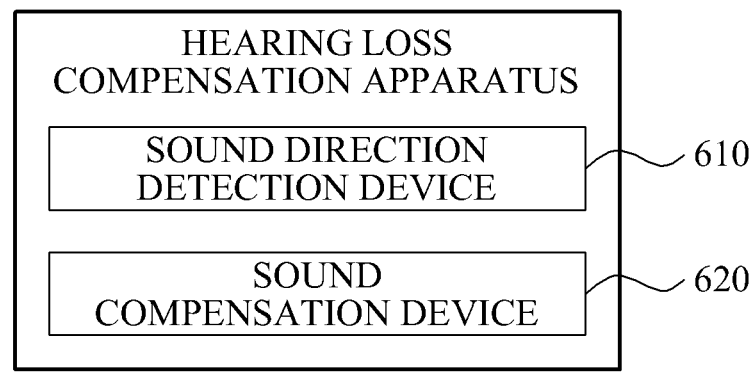
FIG. 6 is a diagram illustrating a configuration of an example of a hearing loss compensation apparatus, according to an example embodiment.

FIG. 6 illustrates a configuration of an example of a hearing loss compensation apparatus 120, according to an example embodiment.

Referring to FIG. 6, in this embodiment the hearing loss compensation apparatus 120 includes a sound direction detection device 610 and a sound compensation device 620.

For example, the sound direction detection device 610 detects a sound generation direction using a plurality of microphones. For example, the sound direction detection device 610 compares amplitudes of sounds detected by the microphones and detects the sound generation direction according to a comparison result. For example, because sounds generated in different directions have different characteristics when received, such characteristics are used to infer the sources of such sounds. In another embodiment, only one microphone is used, and other techniques are used to determine the direction of the sound.

The sound compensation device 620 compensates the sound using hearing characteristics of the user corresponding to the sound generation direction of the sound detected by the sound direction detection device 610.

Thus, the sound compensation device 620 determines the hearing characteristics of the user by comparing hearing abilities of the user at the azimuths and average hearing abilities of other users at the respective azimuths, and amplify the sound based on a characteristic, among the hearing characteristics of the user, that corresponds to an azimuth corresponding to the sound generation direction. Here, the other users refer to users not wearing the hearing loss compensation apparatus 120. That is, in an embodiment average hearing abilities of a population of other users may be hearing abilities of normal users. Such a population potentially includes other users that may have demographic characteristics in common with the user wearing the hearing loss compensation apparatus 120. For example, the population may include individuals of the same gender or age as the individual wearing the hearing loss compensation apparatus 120, who are considered to have normal hearing characteristics.

For example, the hearing characteristics with respect to the front of the user may be lower than the hearing characteristics of the normal users as shown in Case 3 of FIG. 4. In this example, when the sound generation direction is the front of the user, the sound compensation device 620 compensates the sound based on Case 3 of FIG. 4, so that the user correctly recognizes the sound generation direction. For example, the compensation device 620 compensates the sound by increasing its magnitude, to take into account that the user of the compensation device 620 cannot hear as well in that direction as a user with normal hearing.

Figure 7:
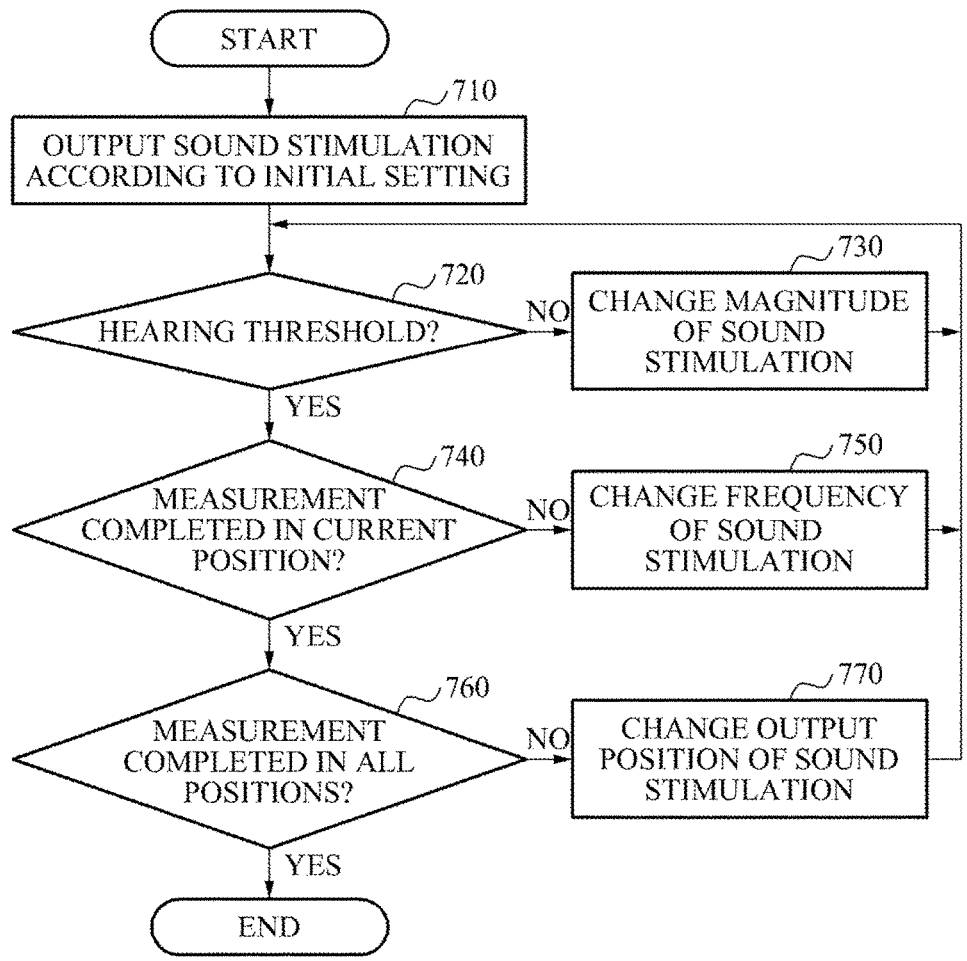
FIG. 7 is a diagram illustrating an example of a hearing characteristic measurement method, according to an example embodiment.

FIG. 7 illustrates an example of a hearing characteristic measurement method.

In operation 710, the method outputs a sound stimulation according to an initial setting. For example, the sound stimulation output device 210 outputs a sound stimulation according to initial setting in a noiseless space. In this example, the initial setting includes a magnitude, a frequency, and an output position of the sound stimulation. For example, the sound stimulation output device 210 outputs the sound stimulation of a predetermined frequency in front of the user.

In operation 720, the method confirms whether the magnitude of the sound stimulation is a hearing threshold of the user. For example, the hearing threshold measurement device 222 confirms whether the magnitude of the sound stimulation is a hearing threshold of the user.

Thus, in an example, when the user inputs that he or she has not perceived the output sound stimulation, the hearing threshold measurement device 222 measures the magnitude of the output sound stimulation as the hearing threshold of the user corresponding to the output position and the frequency of the initial setting, and accordingly performs operation 740.

Conversely, when the user inputs that he or she has perceived the output sound stimulation, the hearing threshold measurement device 222 measures the magnitude of the sound stimulation as not being the hearing threshold and performs operation 730.

In operation 730, the method changes the magnitude of the sound stimulation. For example, the sound stimulation change device 221 changes the magnitude of the sound stimulation output by the sound stimulation output device 210. Here, the hearing threshold measurement device 222 may confirm whether the changed magnitude of the sound stimulation is the hearing threshold of the user, by performing operation 720.

In operation 740, the method confirms whether the measurement is completed in the current position. For example, the hearing threshold measurement device 222 confirms whether the hearing thresholds are measured with respect to all frequencies in a position of the sound stimulation output device 210. At operation 740, the hearing threshold measurement device 222 confirms whether there is a further frequency for measurement of the hearing threshold in the position of the sound stimulation output device 210 besides the frequency at which the hearing threshold is measured.

When there is a frequency at which the hearing threshold is not measured in the position of the sound stimulation output device 210, the sound stimulation change device 221 performs operation 750. When hearing thresholds are measured at all frequencies in the position of the sound stimulation output device 210, the hearing threshold measurement device 222 performs operation 760.

In operation 750, the method changes the frequency of the sound stimulation. For example, the sound stimulation change device 221 changes the frequency of the sound stimulation output by the sound stimulation output device 210. Here, the hearing threshold measurement device 222 confirms whether the magnitude of the sound stimulation of which the frequency is changed is the hearing threshold of the user by performing operation 720.

In operation 760, the method confirms whether the measurement has been completed in all positions. For example, the hearing threshold measurement device 222 confirms whether the hearing thresholds are measured in all positions capable of outputting the sound stimulation. In an example, the positions capable of outputting the sound stimulation are positions corresponding to azimuths of the user. That is, the hearing threshold measurement device 222 confirms whether there is a further azimuth for measurement of the hearing threshold besides the position in which the hearing threshold is measured in operation 740.

When there is a position in which the hearing threshold is not measured among the positions capable of outputting the sound stimulation, the sound stimulation change device 221 performs operation 770. When the hearing thresholds are measured in all the positions capable of outputting the sound stimulation, the method ends. For example, the hearing threshold measurement device 222 ends the method.

In operation 770, the method changes the position from which the sound stimulation is output. For example, the sound stimulation change device 221 changes the position from which the sound stimulation is output. For example, the sound stimulation change device 221 may move the position of the sound stimulation output device 210 and/or may change a sound stimulation output device 210 that outputs the sound stimulation among a plurality of sound stimulation output devices 210. Here, the hearing threshold measurement device 222 performs operation 720 to confirm whether the magnitude of the sound stimulation of which the output position is changed in operation 770 is the hearing threshold of the user.

Furthermore, in another embodiment, an ordering of the operations 720 to 770 may be altered.

For example, the frequency at which the magnitude of the sound stimulation is the hearing threshold may be searched first, by fixing the magnitude of the sound stimulation and changing the frequency as the magnitude is held constant. In addition, alternatively, the hearing thresholds corresponding to azimuths at a particular frequency may be determined first, by fixing the frequency of the sound stimulation while changing the output position of the sound stimulation. Next, the hearing thresholds corresponding to the azimuths per frequency may be determined by changing the frequency.

These methods obtain hearing thresholds in a systematic manner. However, an embodiment may use any method that provides sufficient information about hearing thresholds to allow for hearing threshold compensation.

Figure 8:
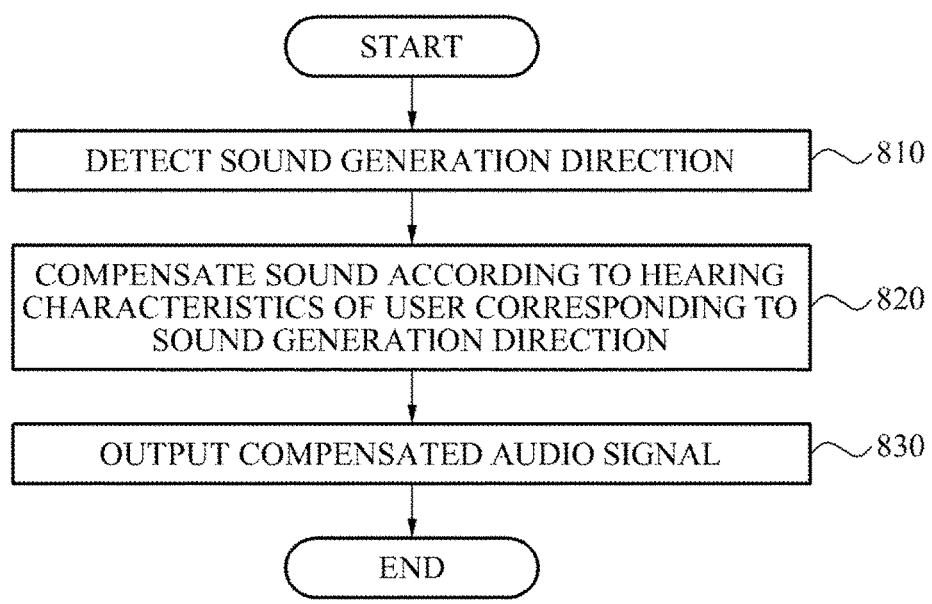
FIG. 8 is a diagram illustrating an example of a hearing loss compensation method, according to an example embodiment.

FIG. 8 illustrates an example of a hearing loss compensation method, according to an example embodiment.

In operation 810, the method detects a sound generation direction. For example, the sound direction detection device 610 detects a sound generation direction in which a sound generates, using a plurality of microphones. In this example, the sound direction detection device 610 compares magnitudes of sounds detected by the respective microphones and detects the sound generation direction according to the comparison result.

In operation 820, the method compensates the sound according to hearing characteristics of a user corresponding to the sound generation direction. For example, the sound compensation device 620 compensate the sound using hearing characteristics of the user, which correspond to the sound generation direction detected by the sound direction detection device 610.

Further, the sound compensation device 620 compares the hearing abilities of the user at the azimuths with average hearing abilities of other users at the respective azimuths, thereby determining hearing characteristics of the user. Also, accordingly, the sound compensation device 620 amplifies the sound based on a characteristic, among the hearing characteristics of the user, that corresponds to an azimuth corresponding to the sound generation direction.

In operation 830, the method outputs a compensated audio signal. For example, the hearing loss compensation apparatus 120 converts the sound compensated in operation 820 into an audio signal and outputs the sound to the user through a speaker or another audio production device.

The examples of a hearing loss compensation apparatus may determine characteristics of hearing deficits for a user with hearing impairment, and provide a hearing loss compensation method based on the characteristics.

The apparatuses and units described herein may be implemented using hardware components. The hardware components may include, for example, controllers, sensors, processors, generators, drivers, and other equivalent electronic components. The hardware components may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

The methods described above can be written as a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more non-transitory computer readable recording mediums. The media may also include, alone or in combination with the software program instructions, data files, data structures, and the like. The non-transitory computer readable recording medium may include any data storage device that can store data that can be thereafter read by a computer system or processing device. Examples of the non-transitory computer readable recording medium include read-only memory (ROM), random-access memory (RAM), Compact Disc Read-only Memory (CD-ROMs), magnetic tapes, USBs, floppy disks, hard disks, optical recording media (e.g., CD-ROMs, or DVDs), and PC interfaces (e.g., PCI, PCI-express, WiFi, etc.). In addition, functional programs, codes, and code segments for accomplishing the example disclosed herein can be construed by programmers skilled in the art based on the flow diagrams and block diagrams of the figures and their corresponding descriptions as provided herein.

A computing system or a computer may include a microprocessor that is electrically connected to a bus, a user interface, and a memory controller, and may further include a flash memory device. The flash memory device may store N-bit data via the memory controller. The N-bit data may be data that has been processed and/or is to be processed by the microprocessor, and N may be an integer equal to or greater than 1. If the computing system or computer is a mobile device, a battery may be provided to supply power to operate the computing system or computer. It will be apparent to one of ordinary skill in the art that the computing system or computer may further include an application chipset, a camera image processor, a mobile Dynamic Random Access Memory (DRAM), and any other device known to one of ordinary skill in the art to be included in a computing system or computer. The memory controller and the flash memory device may constitute a solid-state drive or disk (SSD) that uses a non-volatile memory to store data.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A hearing loss compensation apparatus, comprising:
a sound direction detection device configured to detect, using a microphone, a sound generation direction from which a sound is generated; and
a sound compensation device configured to amplify the sound based on hearing characteristics of a user corresponding to the sound generation direction and comprising an equal loudness contour of the user, in response to detecting a difference between the equal loudness contour of the user and a reference equal loudness contour,
wherein the equal loudness contour of the user is determined by mapping hearing thresholds corresponding to azimuths and frequencies,
wherein the equal loudness contour of the user exists in 3D space comprising a first axis corresponding to the azimuths, a second axis corresponding the frequencies, and a third axis corresponding to the hearing thresholds,
wherein the sound compensation device is further configured to determine the hearing characteristics of the user by comparing hearing abilities of the user at the azimuths and average hearing abilities of other users at the respective azimuths, and amplify the sound based on a characteristic, among the hearing characteristics of the user, that corresponds to an azimuth corresponding to the sound generation direction, and
wherein the other users share a common demographic characteristic with the user.

2. The hearing loss compensation apparatus of claim 1, wherein:
wherein
a hearing threshold among the hearing thresholds is a minimum magnitude of sound audible by the user at an azimuth and a frequency, and
the minimum magnitude of sound is measured by moving a position of a sound stimulation and by controlling a frequency and a magnitude of the sound stimulation.

3. A hearing loss compensation method, comprising:
detecting a sound generation direction, using a microphone, from which a sound is generated; and
amplifying the sound based on hearing characteristics of a user corresponding to the sound generation direction and comprising an equal loudness contour of the user, in response to detecting a difference between the equal loudness contour of the user and a reference equal loudness contour,
wherein the equal loudness contour of the user is determined by mapping hearing thresholds corresponding to azimuths and frequencies,
wherein the equal loudness contour of the user exists in 3D space comprising a first axis corresponding to the azimuths, a second axis corresponding the frequencies, and a third axis corresponding to the hearing thresholds,
wherein the amplifying of the sound comprises determining the hearing characteristics of the user by comparing hearing abilities of the user at the azimuths and average hearing abilities of other users at the respective azimuths, and amplifying the sound based on a characteristic among the hearing characteristics of the user, that corresponds to an azimuth corresponding to the sound generation direction, and
wherein the other users share a common demographic characteristic with the user.

4. The hearing loss compensation method of claim 3, wherein
a hearing threshold among the hearing thresholds is a minimum magnitude of sound audible by the user at an azimuth and a frequency, and
the minimum magnitude of sound is measured by moving a position of a sound stimulation and controlling a frequency and a magnitude of the sound stimulation.

5. A non-transitory computer-readable medium storing instructions that, when executed by one or more processors, cause the one or more processors to implement the method of claim 3.

6. The apparatus of claim 1, wherein the other users are a same age as the user.

7. The apparatus of claim 1, wherein the other users are a same gender as the user.

* * * * *